(12) United States Patent
Pohl et al.

(10) Patent No.: US 7,965,926 B2
(45) Date of Patent: Jun. 21, 2011

(54) CHEMICAL HEATING ASSEMBLY

(75) Inventors: Jeff Pohl, Fort Wayne, IN (US); Robert G. Cox, Kalamazoo, MI (US)

(73) Assignee: Group Dekko, Inc., Kendallville, IN (US)

( * ) Notice: Subject to any disclaimer, the term of this patent is extended or adjusted under 35 U.S.C. 154(b) by 673 days.

(21) Appl. No.: 12/025,088

(22) Filed: Feb. 4, 2008

(65) Prior Publication Data

US 2009/0196585 A1  Aug. 6, 2009

(51) Int. Cl.
*F24F 6/00* (2006.01)
*F22B 1/20* (2006.01)

(52) U.S. Cl. .......................... 392/392; 392/386
(58) Field of Classification Search .......... 392/386–406; 165/53, 54
See application file for complete search history.

(56) References Cited

U.S. PATENT DOCUMENTS

| | | | |
|---|---|---|---|
| 3,088,087 A | 4/1963 | Colten | 339/18 |
| 3,111,641 A | 11/1963 | Wilentchik | 338/221 |
| 3,201,617 A | 8/1965 | Pacoroni et al. | 307/146 |
| 4,846,701 A | 7/1989 | Hayes et al. | 439/620 |
| 4,849,606 A | 7/1989 | Martens, III et al. | 219/271 |
| 5,213,523 A | 5/1993 | Hygema et al. | 439/620 |
| 5,521,357 A | 5/1996 | Lock et al. | 219/543 |
| 5,937,140 A | 8/1999 | Leonard et al. | 392/392 |
| 6,085,026 A | 7/2000 | Hammons et al. | 392/390 |
| 6,102,031 A * | 8/2000 | Waters | 126/92 AC |
| 6,478,440 B1 | 11/2002 | Jaworski et al. | |
| 6,862,403 B2 * | 3/2005 | Pedrotti et al. | 392/395 |
| 7,352,960 B2 * | 4/2008 | Hafer et al. | 392/395 |
| 2001/0053283 A1 * | 12/2001 | Levine et al. | 392/395 |
| 2002/0172512 A1 * | 11/2002 | Stathakis et al. | 392/395 |
| 2003/0194225 A1 * | 10/2003 | Pedrotti et al. | 392/395 |

* cited by examiner

*Primary Examiner* — Daniel Robinson
(74) *Attorney, Agent, or Firm* — Taylor IP

(57) ABSTRACT

A chemical heating assembly includes a face plate, a chemical packet, a housing, a pair of electrical prongs carried by the housing, and a light assembly. The housing includes a first sliding arrangement and a first snap-fit arrangement, is connected to the face plate, and at least partially defines a pocket for the chemical packet. The light assembly includes a lamp, a second sliding arrangement engaged with the first sliding arrangement, and a second snap-fit arrangement coupled with the first snap-fit arrangement. The light assembly is mechanically connected to the housing and electrically connected with the pair of electrical prongs using the first and second sliding arrangements and the first and second snap-fit arrangements.

6 Claims, 5 Drawing Sheets

CHEMICAL HEATING ASSEMBLY

BACKGROUND OF THE INVENTION

1. Field of the Invention

The present invention relates to heating assemblies, and, more particularly, to chemical heating assemblies such as chemical vaporizers.

2. Description of the Related Art

Electrically heated vapor dispensing apparatuses can be plugged into a conventional electrical outlet of a building and can be used, for example, to dispense a fragrance, an insect repellant, or vapors for health care purposes into the air surrounding chemical heating assembly. An electrically heated vapor dispensing apparatus is known which includes a heater portion and a light assembly, the heater portion including a heater base with a heating element. To obtain a secure connection therebetween, the heater base and the light assembly are overmolded together.

What is needed in the art is a chemical heating assembly including a housing, which can carry a heating device, and a light assembly which mechanically and electrically couple securely together using sliding and snap-fit arrangements.

SUMMARY OF THE INVENTION

The present invention provides a chemical heating assembly including a housing, which can carry a heating device, and a light assembly which mechanically and electrically couple securely together using sliding and snap-fit arrangements.

The invention in one form is directed to a chemical heating assembly including a face plate, a chemical packet, a housing, a pair of electrical prongs carried by the housing, and a light assembly. The housing includes a first sliding arrangement and a first snap-fit arrangement, is connected to the face plate, and at least partially defines a pocket for the chemical packet. The light assembly includes a lamp, a second sliding arrangement engaged with the first sliding arrangement, and a second snap-fit arrangement coupled with the first snap-fit arrangement. The light assembly is mechanically connected to the housing and electrically connected with the pair of electrical prongs using the first and second sliding arrangements and the first and second snap-fit arrangements.

The invention in another form is directed to a heating assembly including a housing, a pair of electrical prongs carried by the housing, and a light assembly. The housing includes a first sliding arrangement and a first snap-fit arrangement. The light assembly includes a lamp, a second sliding arrangement engaged with the first sliding arrangement, and a second snap-fit arrangement coupled with the first snap-fit arrangement. The light assembly is mechanically connected to the housing and electrically connected with the pair of electrical prongs using the first and second sliding arrangements and the first and second snap-fit arrangements.

The invention in yet another form is directed to a method of assembling a chemical heating assembly. The method includes the step of providing a housing, a light assembly including a lamp, and a pair of electrical prongs carried by the housing, the housing at least partially defining a pocket for a chemical packet. The method further includes the steps of mechanically connecting the light assembly to the housing and electrically connecting the light assembly with the pair of electrical prongs by sliding the light assembly and the housing relative to one another and snap-fitting the light assembly and the housing together.

An advantage of the present invention is that sliding and snap-fit arrangements securely couple, mechanically and electrically, the housing and the light assembly.

Another advantage is that overmolding is not necessary to securely couple, mechanically and electrically, the housing and the light assembly together.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one embodiment of the invention, and such exemplifications are not to be construed as limiting the scope of the invention in any manner.

DETAILED DESCRIPTION OF THE INVENTION

Figure 1:
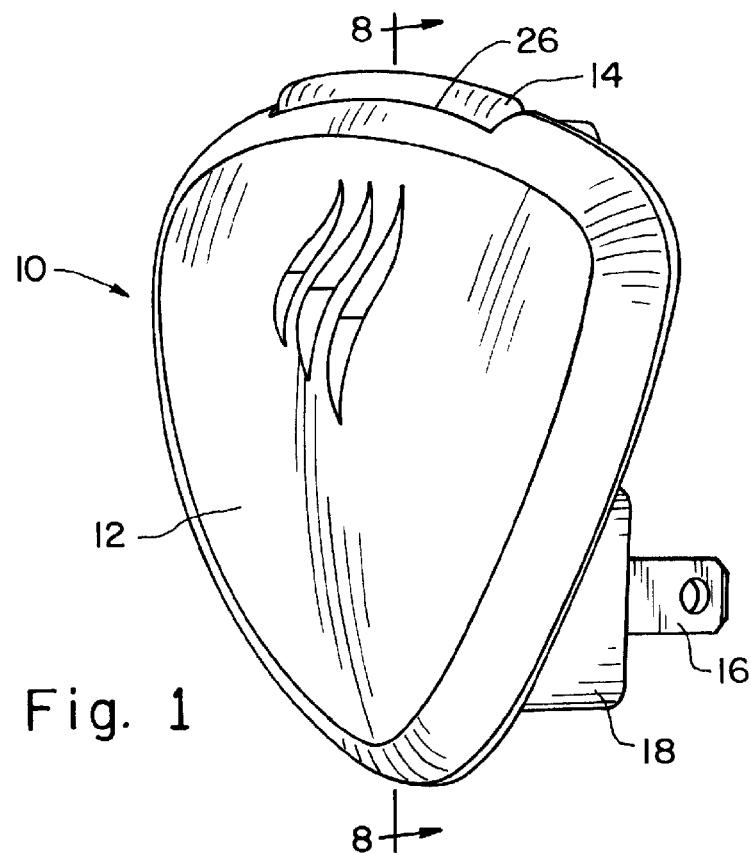
FIG. 1 is a front perspective view of the chemical heating assembly according to the present invention with the chemical packet, the light assembly being fully engaged with the housing.
Figure 2:
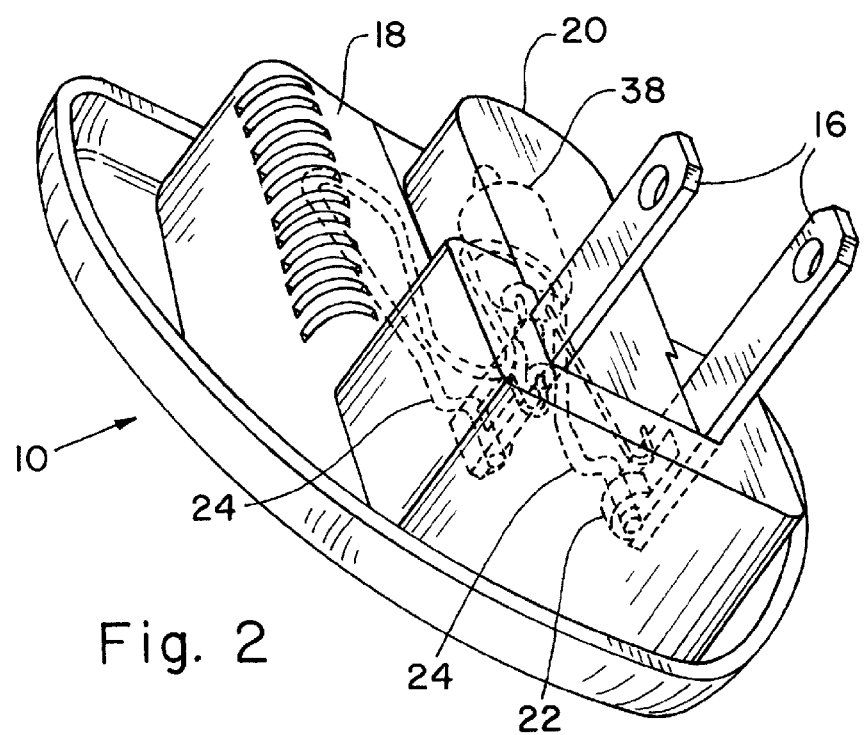
FIG. 2 is a rear perspective view of the chemical heating assembly according to the present invention without the chemical packet but with portions in broken lines.
Figure 3:
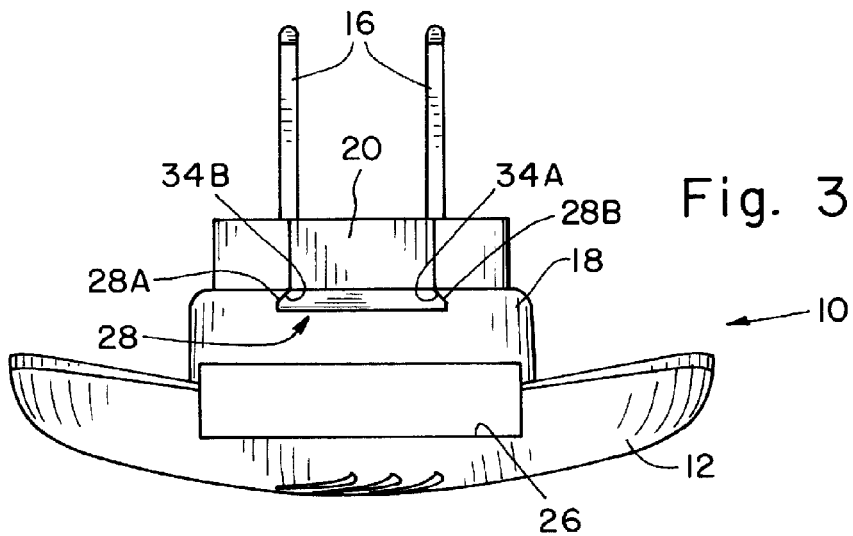
FIG. 3 is top view of the chemical heating assembly according to the present invention without the chemical packet.

Referring now to the drawings, and more particularly to FIGS. 1-3, there is shown a heating assembly 10, such as a chemical heating assembly 10, which generally includes a face plate 12, a chemical packet 14, a pair of electrical prongs 16, a housing 18, and a light assembly 20. Chemical heating assembly 10 can be plugged into a conventional electrical outlet of a building and be used, for example, to light an area and dispense air deodorizers, insect repellants, vapors for health care purposes, or other suitable substances into the air surrounding chemical heating assembly 10.

Face plate 12 provides an aesthetically pleasing covering over the front of heating assembly 10. Face plate 12 can be configured for diffusing a deodorizing vapor emanating from chemical packet 14 and/or for diffusing and/or reflecting light from light assembly 20. Chemical packet 14 is filled with any suitable air treating material, such as an air deodorizer, an insect repellent, a health care agent, or the like. After heating assembly 10 is plugged into an outlet, chemical packet 14 can be heated so as to cause the air deodorizer, for example, to be released into the air surrounding heating assembly 10. Chemical packet 14 can be a fungible item during use in that an end-user can replace the current chemical packet 14 with a new chemical packet 14 when the current chemical packet 14 no longer emits the air deodorizer, for example.

Electrical prongs 16 are carried by housing 18 a fixed distance apart from one another. Electrical prongs 16 can be overmolded with housing 18 during the formation of housing 18 so as to be partially encapsulated by housing 18, which can be made of an electrically insulating material. Electrical prongs 16 are configured for mechanically and electrically engaging a conventional electrical outlet of a building. Each electrical prong 16 can form a tab 22 which securely holds a respective end of a heating device 24, such as a heater wire 24, using a crimping press (see FIGS. 2 and 4).

Housing 18 is connected to face plate 12 and at least partially defines a pocket 26 for chemical packet 14. More specifically, housing 18 and face plate 12 can together define pocket 26 which slidably receives chemical packet 14. Housing 18 can be formed monolithic with face plate 12 or be formed separately from face plate 12 and subsequently attached to face plate 12. Housing 18 includes a first sliding arrangement 28 and a first snap-fit arrangement 30. First sliding arrangement 28 can include, for example, a female dovetail 28, as shown in FIG. 3. More specifically, female dovetail 28 can include two angular recesses 28A and 28B defined by housing 18, each angular recess 28A,28B having an open face which generally faces the open face of the other angular recess 28A,28B. Further, each angular recess 28A, 28B can extend longitudinally along a backside of housing 18 such that each angular recess 28A,28B runs generally in a top to bottom direction of housing 18. Each angular recess 28A, 28B may start at the top of housing 18 and extend only partially along the longitudinal length of housing 18.

Figure 8:
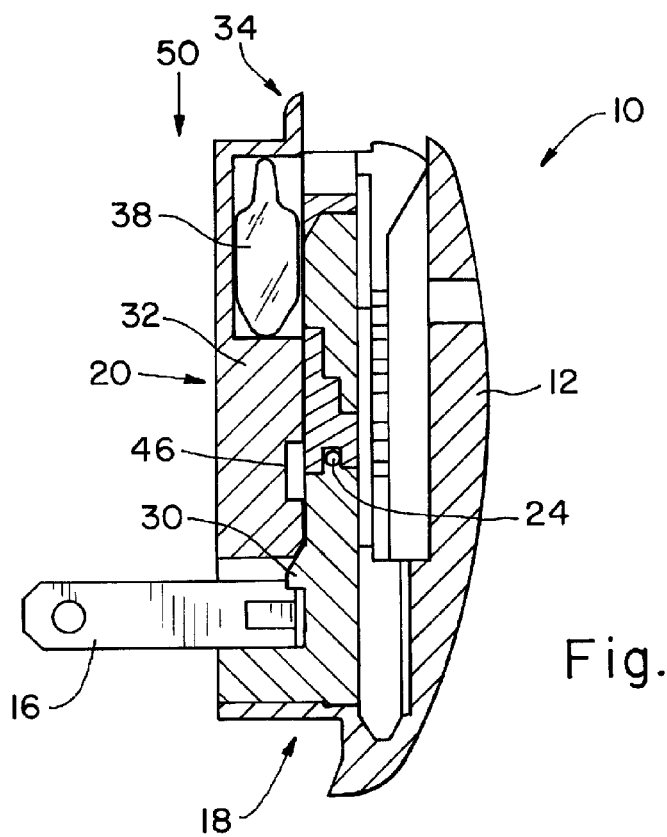
FIG. 8 is a cross-sectional view of the chemical heating assembly according to the present invention, the cross-sectional view being taken along line 8-8 in FIG. 1 (without the chemical packet) but showing the light assembly sliding along housing just as the light assembly begins to engage the ramped projection of housing.
Figure 9:
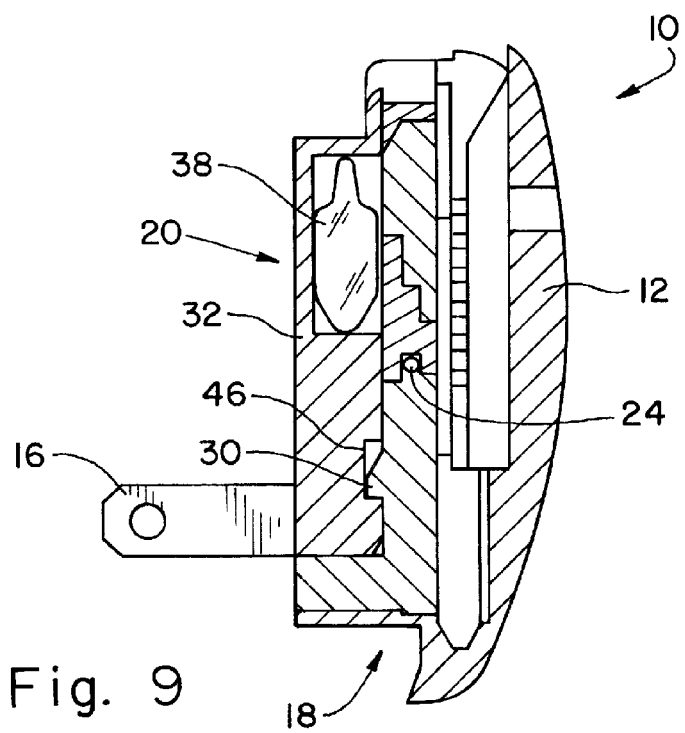
FIG. 9 is a cross-sectional view of the chemical heating assembly according to the present invention showing the light assembly fully engaged with the housing (without the chemical packet), the cross-sectional view being taken along line 8-8 in FIG. 1.

First snap-fit arrangement 30 can include, for example, a ramped projection 30, as shown in FIGS. 8-9. More specifically, ramped projection 30 can be positioned on a back wall of housing, in the bottom half portion of the back wall, and generally centered transversely (the transverse direction of heating assembly 10 runs perpendicular to the top to bottom direction of housing 18). Ramped projection 30 can slope away from the back wall of housing 18 running generally in a top to bottom direction of housing 18 and include a top section which is generally parallel to the back wall of housing 18.

Housing 18 carries heating device 24 which is configured for heating up as electrical current passes through heating device 24 so as to heat up chemical packet 14, which releases the air deodorizer upon being heated up. The opposing ends of the heater wire 24, which can be a heater wire 24, can be secured to tabs 22 of electrical prongs 16 and deformed by the crimping press when forming a tight connection with tabs 22. As a result, heating device 24 is electrically coupled with the pair of electrical prongs 16. Heater wire 24 and a portion of electrical prongs 16 can be overmolded. That is, heater wire 24 and electrical prongs 16 are loaded into a mold with the ends of heater wire 24 situated in tabs 22 of electrical prongs 16, and plastic, for instance, can then be shot around heater wire 24 and a portion of electrical prongs 16 so that heater wire 24 and the crimp connection portion of electrical prongs 16 become completely encapsulated in plastic. As a result, housing 18 is formed and encapsulates heater wire 24 and the crimp connection portion of electrical prongs 16. In this way, the position of heater wire 24 and electrical prongs 16 in housing 18 is controlled.

Light assembly 20, as shown in FIGS. 4-9, can serve as a night light which can emit light when electrical prongs 16 are plugged into a building outlet. Light assembly 20 includes a lens 32, a second sliding arrangement 34 formed on lens 32 and engaged with first sliding arrangement 28, a second snap-fit arrangement 36 formed on lens 32 and coupled with first snap-fit arrangement 30, a lamp 38, and a pair of electrical leads 40. Light assembly 20, using lens 32, couples with the backside of housing 18. Light assembly 20 is mechanically connected to housing 18 and electrically connected with the pair of electrical prongs 16 using first and second sliding arrangements 28,34 and first and second snap-fit arrangements 30,36. That is, in coupling light assembly 20 with housing 18, second sliding arrangement 34 is engaged with first sliding arrangement 28 and second snap-fit arrangement 36 is coupled with first snap-fit arrangement 30. In so coupling, light assembly 20 is slidably received by housing 18, as indicated in FIGS. 8 and 9. FIG. 8 shows light assembly 20 sliding into place relative to housing 18 in the direction of arrow 50. FIG. 9 shows light assembly 20 seated in place relative to housing 18.

Lens 32 can be made of a transparent or semi-transparent material so that the light from lamp 38 is able to shine therethrough. Lens 32 carries lamp 38 and electrical leads 40 and can define an open front side which faces housing 18 when coupled thereto and through which lamp 38 and electrical leads 40 can be set and secured to lens 32 during manufacturing. Lens 32 further includes a centrally located, longitudinally extending wall 42 (also called a rib 42) formed on and projecting generally perpendicularly from a back wall of lens 32. Lens 32 further includes a pair of bulges 44 one of which is formed on the bottom of each exterior side of lens 32. Rib 42 facilitates holding lamp 38 in place in lens 32 and can work in cooperation with side walls of lens 32 to hold lamp 38, as well as electrical leads 40 (effectively trapping leads 40), in place.

Figure 4:
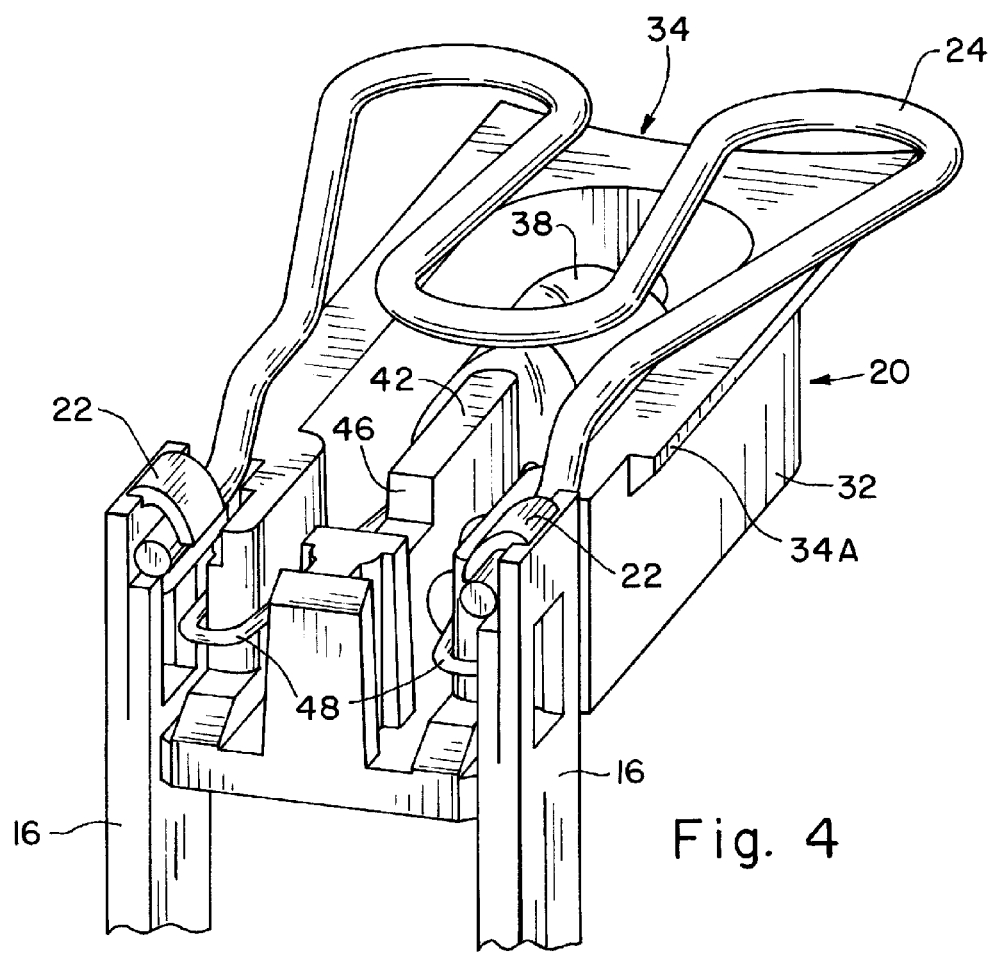
FIG. 4 is a perspective view of the electrical connections of the chemical heating assembly according to the present invention with the housing, faceplate, and chemical packet broken away.
Figure 5:
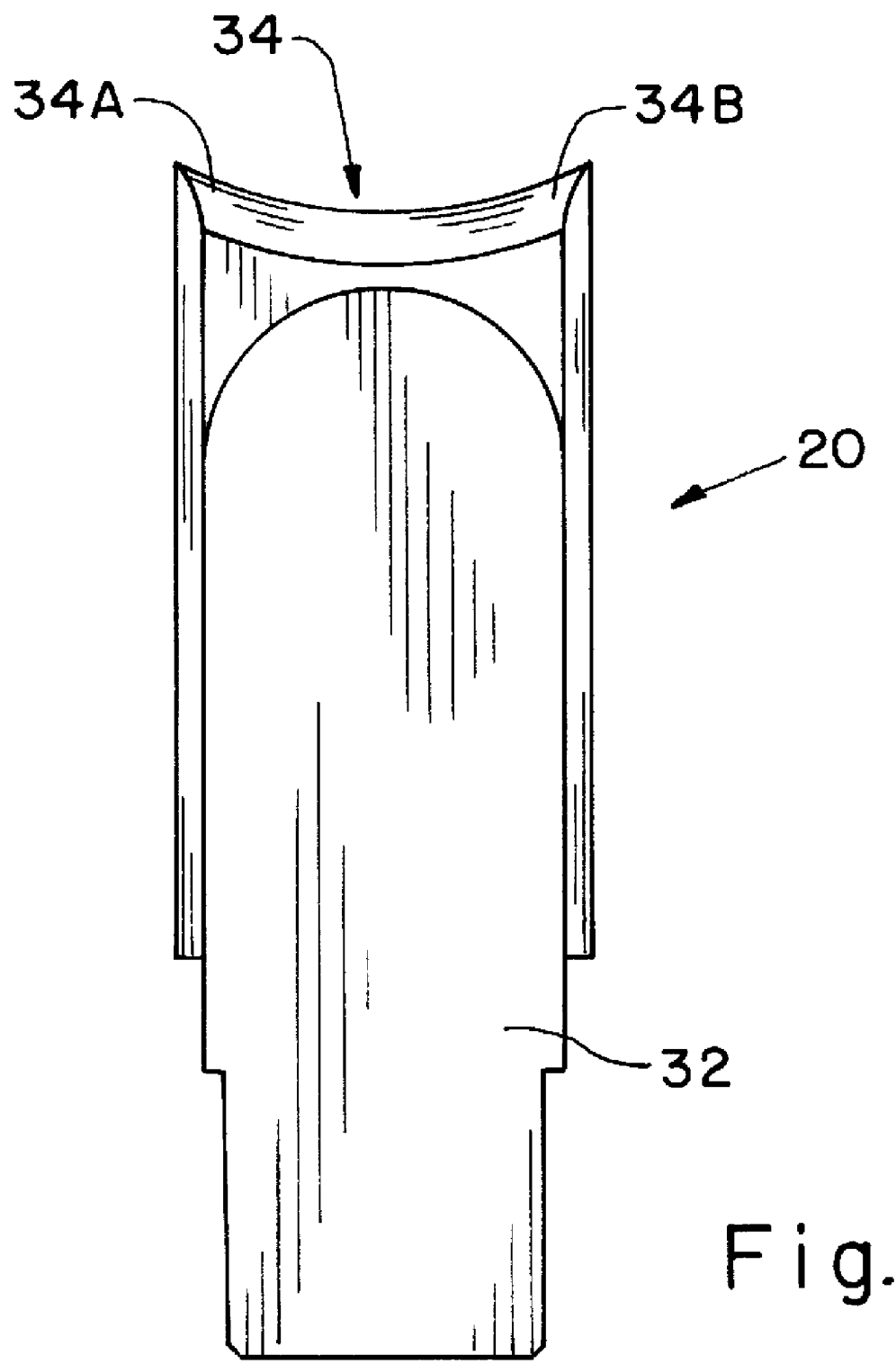
FIG. 5 is a back side view of the lens broken away from remaining portions of the chemical heating assembly according to the present invention.
Figure 6:
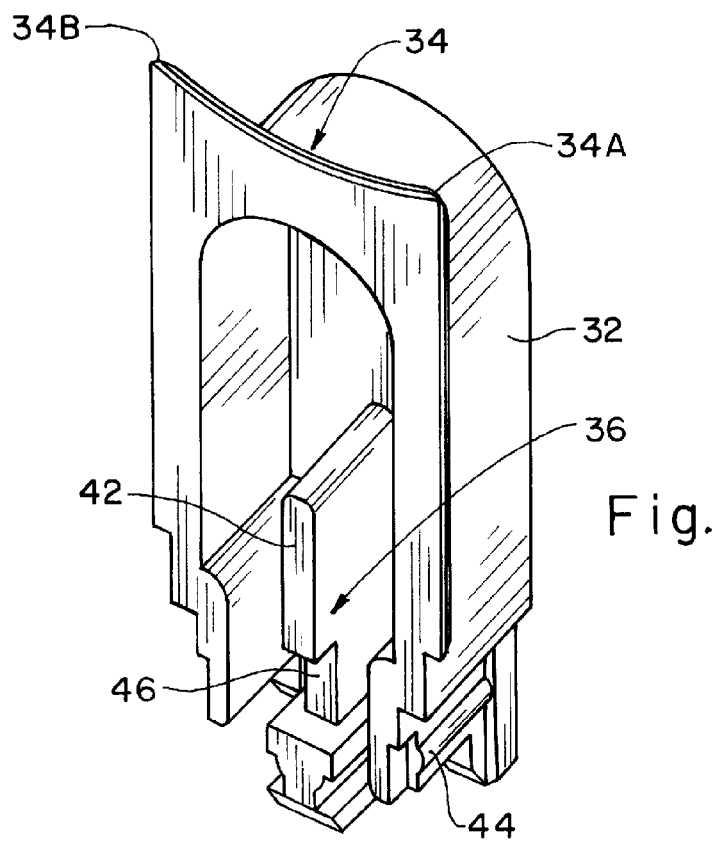
FIG. 6 is a perspective view of the lens broken away from remaining portions of the chemical heating assembly according to the present invention.

Second sliding arrangement 34 can include, for example, a male dovetail 34 formed on lens 32, as shown in FIGS. 3-7. More specifically, male dovetail 34 can include two angular projections 34A and 34B defined by lens 32, angular projections 34A,34B generally facing in opposite directions relative to one another. Further, each angular projection 34A,34B can extend longitudinally along a front side of lens 32 such that each angular projection 34A,34B runs generally in a top to bottom direction of lens 32. Each angular projection 34A,34B may start at the top of lens 32 and extend only partially along the longitudinal length of lens 32, as shown in FIGS. 4-6. Male dovetail 34 is shaped to matingly fit with female dovetail 28; that is, angular projections 34A,34B of male dovetail 34 matingly correspond to angular recesses 28A,28B of female dovetail 28. Accordingly, female dovetail 28 of housing 18 can slidably receive male dovetail 34 of lens 32, as shown in FIG. 3.

Second snap-fit arrangement 36 can include, for example, rib 42 defining a recess 46, as shown in FIGS. 4, 6-9. More specifically, recess 46 can be positioned at or near the bottom of rib 42 running in a top to bottom direction of rib 42, which is generally centered between longitudinal sides of lens 32. Recess 46 can be a cutout 46 having a generally square or rectangular cross section. That is, recess 46 can have generally parallel first and second walls and a third wall extending therebetween, the first and second walls being generally perpendicular to the back wall of lens 32. Recess 46 is configured to receive ramped projection 30 therein such that ramped projection 30 snap-fits in recess 46. Recess 46 and ramped projection 30 cooperate to inhibit an upward movement of lens 32 relative to housing 18. The lens 32 and housing 18, thus, cooperate together such that a tight fit is formed therebetween. The lens 32 may not be removable from housing 18 after initial installation, during normal use; in such a design, lamp 38 would not be replaceable.

Figure 7:
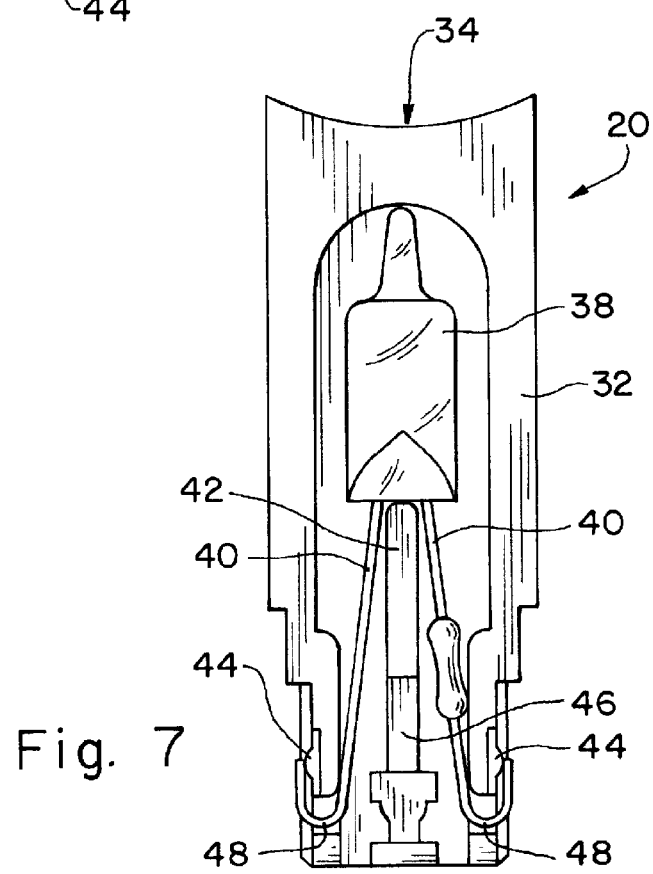
FIG. 7 is a front side view of the light assembly broken away from remaining portions of the chemical heating assembly according to the present invention.

Lamp 38 is configured to emit light, for example, a green-colored light. Electrical leads 40 are respectively coupled with lamp 38. One electrical lead 40 can be the hot line to lamp 38, while the other electrical lead 40 can be the neutral line from lamp 38. The electrical lead 40 which serves as the hot line can be coupled with a voltage dropping resistor, as shown in FIGS. 4 and 7. Further, each electrical lead 40 can include a hooked section 48, as shown in FIGS. 2, 4, and 7. During installation, lamp 38 and electrical leads 40 are set in lens 32, lamp 38 being held in place by rib 42 and electrical leads 40 being trapped between rib 42 and side walls of lens 32. The hooked section 48 of each electrical lead 40 wraps around the bottom of the side walls of lens 32, the distal end of each hooked section 48 contacting bulges 44 of each side wall of lens 32. Thus, at least a portion of each hooked section 48 is exposed outside of lens 32. In coupling light assembly 20 with housing 18, electrical leads 40 are respectively frictionally engaged with electrical prongs 16. More specifically, the exposed portions of the hooked sections 48 of electrical leads 40 frictionally engage with exposed portions of electrical prongs 16 when light assembly is coupled and seated with housing 18. That is, the exposed portions of electrical leads 40 directly contact the respectively exposed portions of electrical prongs 16 so as to make an electrical connection between electrical leads 40 and electrical prongs 16. Bulges 44 on lens 32 respectively push distal ends of electrical leads 40 to touch electrical prongs 16.

In use, the present invention also provides a method of assembling chemical heating assembly 10. The method includes providing housing 18, light assembly 20 including lamp 38, and the pair of electrical prongs 16 carried by housing 18, housing 18 at least partially defining pocket 26 for chemical packet 14. The method also includes mechanically connecting light assembly 20 to housing 18 and electrically connecting light assembly 20 with the pair of electrical prongs 16 by sliding light assembly 20 and housing 18 relative to one another and snap-fitting light assembly 20 and housing 18 together. The method can further include coupling the pair of electrical leads 40 of light assembly 20 respectively with lamp 38 and frictionally engaging the pair of electrical leads 40 respectively with the pair of electrical prongs 16. Light assembly 20 can be slidably received by housing 18. Light assembly 20 can include a male dovetail 34, and housing 18 can include a female dovetail 28 which slidably receives male dovetail 34. Ramped projection 30 of housing 18 can be snap-fit in recess 46 defined by wall 42 of light assembly 20. The method can also provide heating device 24 carried by housing 18 and electrically coupled with the pair of electrical prongs 16. As such, light assembly 20 can be mounted to housing 18 by sliding light assembly 20 relative to housing 18 using male and female dovetails 34,28. In so sliding, rib 42 of lens 32 eventually slides up the ramp of ramped projection 30 until ramped projection 30 snaps into recess 46. The bottom corner of rib 42 is the leading edge of rib 42 when sliding down housing 18 and initially contacts the ramp of ramped projection 30; this bottom corner of rib 42 can include a beveled surface so as to facilitate sliding of rib 42 up the ramp of ramped projection 30. When ramped projection 30 snap-fits to recess 46, light assembly 20 is mechanically secured to housing 18 and electrical leads 40 are electrically connected to and respectively in direct contact with electrical prongs 16.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A chemical heating assembly comprising:
a face plate;
a chemical packet;
a housing including a first sliding arrangement and a first snap-fit arrangement, said housing connected to said face plate and at least partially defining a pocket for said chemical packet;
a pair of electrical prongs carried by said housing; and
a light assembly including a lamp, a second sliding arrangement engaged with said first sliding arrangement, and a second snap-fit arrangement coupled with said first snap-fit arrangement, said light assembly mechanically connected to said housing and electrically connected with said pair of electrical prongs using said first and second sliding arrangements and said first and second snap-fit arrangements.

2. The chemical heating assembly of claim 1, wherein said light assembly includes a pair of electrical leads respectively coupled with said lamp and frictionally engaged with said pair of electrical prongs.

3. The chemical heating assembly of claim 1, wherein said light assembly is slidably received by said housing.

4. The chemical heating assembly of claim 3, wherein said second sliding arrangement includes a male dovetail and said first sliding arrangement includes a female dovetail which slidably receives said male dovetail.

5. The chemical heating assembly of claim 1, wherein said first snap-fit arrangement includes a ramped projection and said second snap-fit arrangement includes a wall defining a recess, said ramped projection snap-fitting in said recess.

6. The chemical heating assembly of claim 1, further comprising a heating device carried by said housing and electrically coupled with said pair of electrical prongs.

* * * * *